(12) United States Patent
Ji et al.

(10) Patent No.: US 12,377,261 B2
(45) Date of Patent: Aug. 5, 2025

(54) WATCHBAND WITH CONDUCTIVE FUNCTION OF BRACELET

(71) Applicant: WAT Medical Enterprise Ltd., Jiaxing (CN)

(72) Inventors: Hualei Ji, Ningbo (CN); Haojie Xu, Ningbo (CN); Wufeng Ji, Ningbo (CN)

(73) Assignee: WAT Medical Enterprise Ltd., Jiaxing (CN)

( * ) Notice: Subject to any disclaimer, the term of this patent is extended or adjusted under 35 U.S.C. 154(b) by 855 days.

(21) Appl. No.: 17/405,034

(22) Filed: Aug. 18, 2021

(65) Prior Publication Data

US 2022/0071358 A1 Mar. 10, 2022

(30) Foreign Application Priority Data

Sep. 4, 2020 (CN) .......................... 202010918970.5

(51) Int. Cl.
| | | |
|---|---|---|
| *A61N 1/04* | (2006.01) | |
| *A44C 5/14* | (2006.01) | |
| *A44C 5/20* | (2006.01) | |
| *A61B 5/00* | (2006.01) | |
| *A61B 5/024* | (2006.01) | |
| *G06F 1/16* | (2006.01) | |

(52) U.S. Cl.
CPC ............ *A61N 1/0472* (2013.01); *A44C 5/145* (2013.01); *A44C 5/2071* (2013.01); *A61B 5/02438* (2013.01); *A61B 5/681* (2013.01); *G06F 1/163* (2013.01)

(58) Field of Classification Search
USPC ......................................................... 600/301
See application file for complete search history.

(56) References Cited

U.S. PATENT DOCUMENTS

| | | | |
|---|---|---|---|
| 6,529,754 B2* | 3/2003 | Kondo ............... | A61B 5/02438 600/335 |
| 11,312,047 B2* | 4/2022 | Francois .............. | A44C 5/0007 |
| 2016/0070234 A1* | 3/2016 | Lee .......................... | A44C 5/14 368/282 |
| 2017/0157398 A1* | 6/2017 | Wong ................... | A61B 5/1101 |
| 2018/0103859 A1* | 4/2018 | Provenzano ......... | A61B 5/0024 |
| 2018/0210491 A1* | 7/2018 | Song ................ | G06K 19/07773 |
| 2020/0324104 A1* | 10/2020 | Labuschagne ....... | A61N 5/0622 |

* cited by examiner

*Primary Examiner* — Ahmed M Farah
(74) *Attorney, Agent, or Firm* — Bayramoglu Law Offices LLC

(57) ABSTRACT

A smart bracelet with a conductive watchband includes a first watchband and a second watchband. The inside of the first watchband is provided with an electrical stimulation module. The electrical stimulation module includes a signal strip arranged along the length direction of the first watchband, a circuit board connected to the signal strip and an electrode connected to the circuit board. The electrode is located at an end of the first watchband away from the dial.

7 Claims, 8 Drawing Sheets

WATCHBAND WITH CONDUCTIVE FUNCTION OF BRACELET

CROSS REFERENCE TO THE RELATED APPLICATIONS

This application is based upon and claims priority to Chinese Patent Application No. 202010918970.5, filed on Sep. 4, 2020, the entire contents of which are incorporated herein by reference.

TECHNICAL FIELD

The present disclosure relates to the field of smart bracelet, and in particular, to a smart bracelet with a conductive watchband.

BACKGROUND

With the development of Internet technology and intelligent products, various intelligent wearable products have appeared on the market. Among them, the smart bracelet appears as a common smart wearable product, which brings convenience to users.

The existing smart bracelet generally includes a dial and two watchbands connected to the dial, the dial has the functions of monitoring sleep, heart rate, calorie consumption, etc., the watchband is similar to a wrist strap. One watchband has a buckle, and the other watchband has a row of small holes, the small holes are arranged at intervals, and the buckle can be inserted into any small hole, the user can insert the buckle into the most suitable hole according to the size of the wrist.

The above-mentioned prior art solutions have the following defects: the watchbands are only used to fix the bracelet on the wrist, and the watchbands have fewer functions, so the watchbands need to be further improved.

SUMMARY

A smart bracelet with a conductive watchband is provided, the watchband includes a dial, a first watchband and a second watchband, the first watchband is connected to one end of the dial, the second watchband is connected to the other end of the dial, an inside of the first watchband is provided with an electrical stimulation module, the electrical stimulation module includes a signal strip, a circuit board and an electrode, the circuit board is connected to the signal strip, the electrode is connected to the circuit board, the electrode is located at an end of the first watchband away from the dial.

Further, the signal strip is arranged along a length direction of the first watchband.

Further, the inside of the first watchband is provided with a spring sheet which is arranged along the length direction of the first watchband, the spring sheet is located directly above the signal strip, an insulating layer is spread between the spring sheet and the signal strip.

Further, the inside of the first watchband is provided with an electrode support plate, and the circuit board is located in the electrode support plate, and the spring sheet is located above the electrode support plate.

Further, the circuit board is provided with a pin, a top surface of the electrode support plate is provided with a bottom carriage, the electrode is located on a top surface of the bottom carriage, the pin is configured to pass through the bottom carriage and get in touch with a bottom surface of electrode, the bottom carriage is made of conductive metal.

Further, there are two electrodes, and a sensor for detecting physiological parameters of users is provided between the two electrodes, the sensor is connected to the circuit board.

Further, an inner surface of the first watchband is provided with a groove corresponding to the electrode, a cover plate is provided in the groove, the cover plate is located above the electrode, the cover plate is made of conductive metal.

Further, the first watchband is a buckle-end silicone watchband, the second watchband is a tongue-end silicone watchband, the buckle-end silicone watchband is provided with a buckle, and the tongue-end silicone watchband is provided with several lock holes, the lock holes are equally spaced along a length direction of the tongue-end silicone watchband, and the lock holes are cooperated with the buckle.

Further, a clamping block is provided on an outer surface of the first watchband, the clamping block is cooperated with one of the lock holes.

Further, a limiting ring is sleeved on the first watchband, the limiting ring is for inserting the second watchband.

In the figures: 1. dial; 2. first watchband; 21. buckle; 22. groove; 23. limiting ring; 3. second watchband; 31. lock hole; 4. signal strip; 5. circuit board; 6. electrode; 61. cover plate; 7. spring sheet; 71. insulating layer; 8. electrode support plate; 81. bottom carriage; 9. clamping block; 10. sensor.

DETAILED DESCRIPTION OF THE EMBODIMENTS

The preferred embodiments of the present disclosure will be described in detail below in conjunction with the accompanying drawings, so that the advantages and features of the present disclosure can be more easily understood by those skilled in the art, therefore, the protection scope of the present disclosure is defined more clearly.

The First Embodiment

Figure 1:
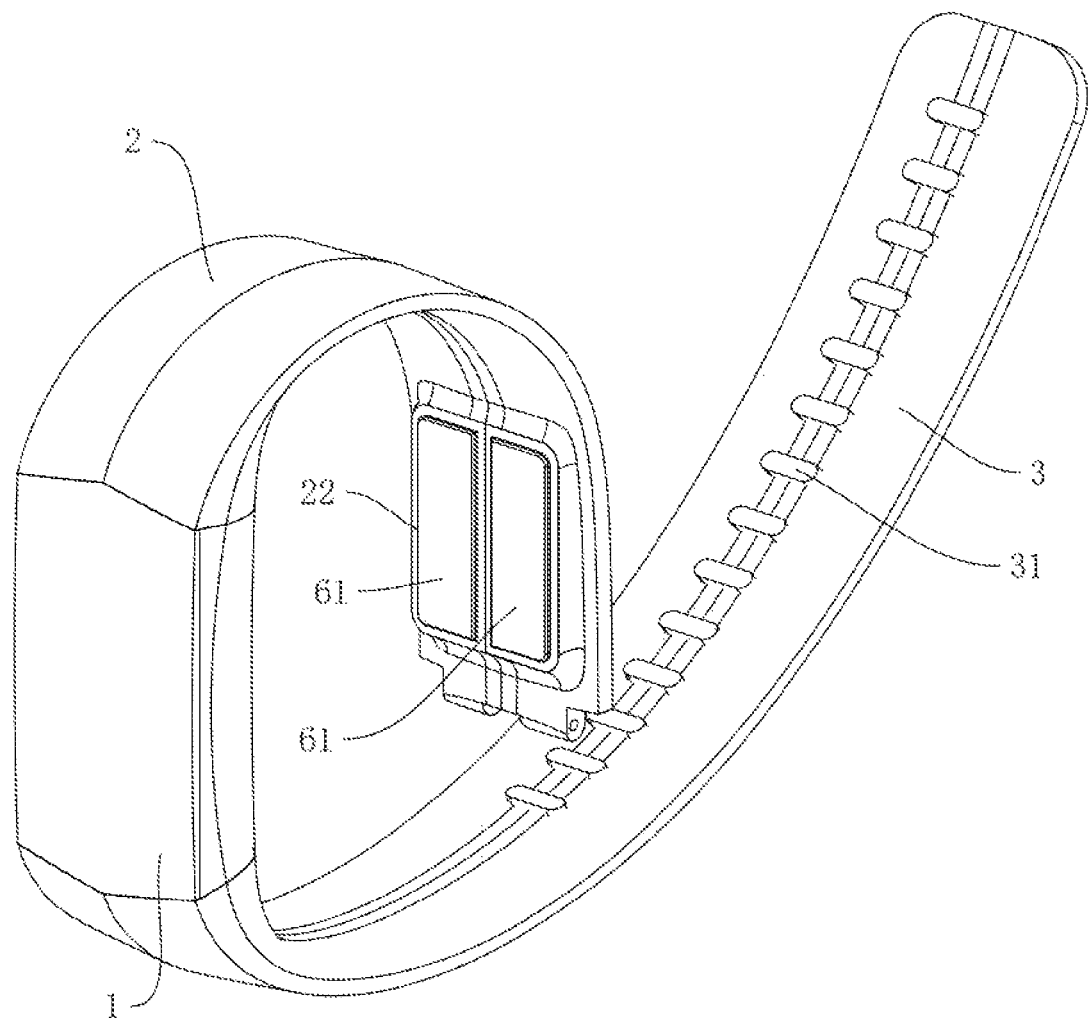
FIG. 1 is a schematic structural diagram of a bracelet when a buckle-end silicone watchband is in a bent state.
Figure 2:
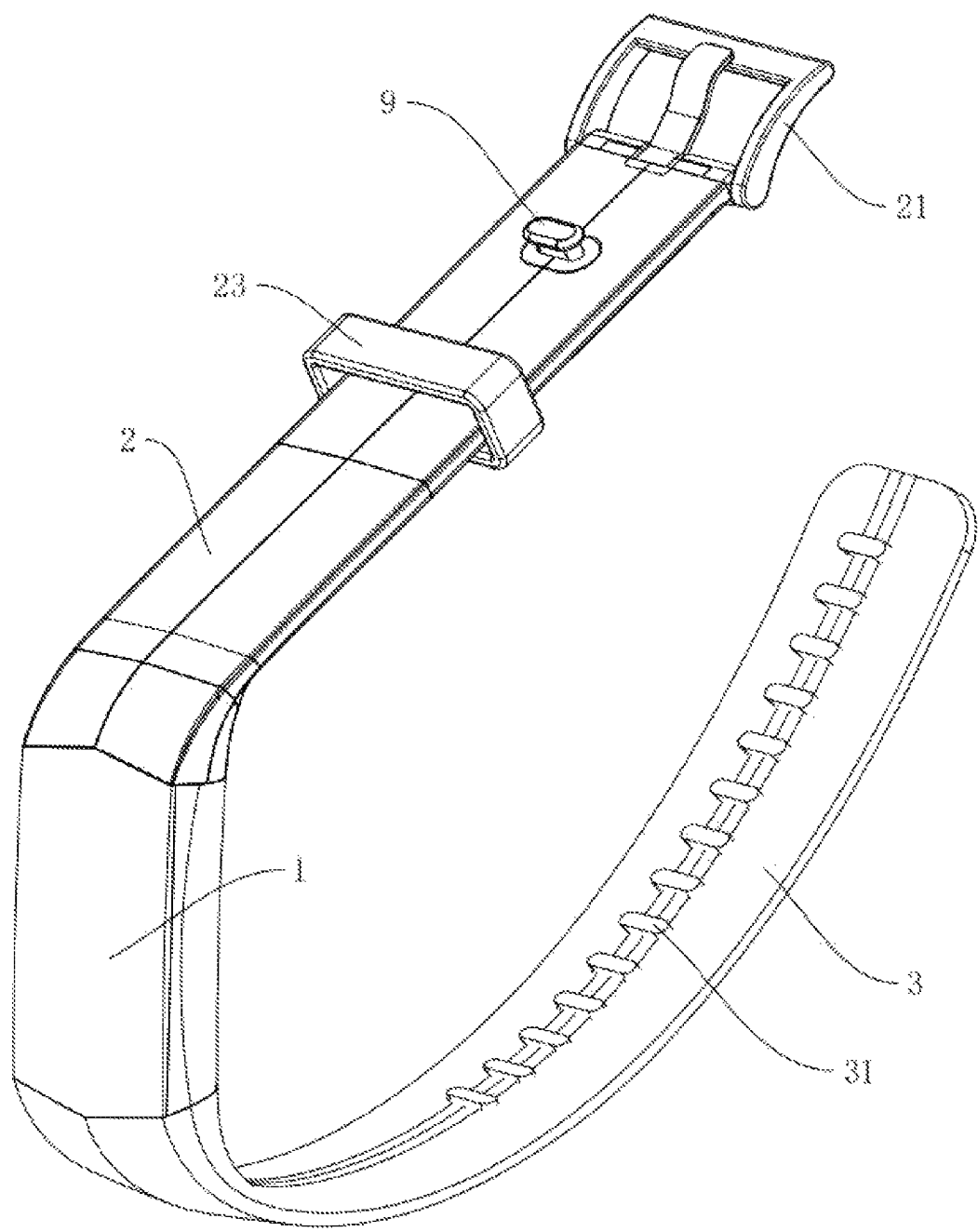
FIG. 2 is a schematic structural diagram of a bracelet when the buckle-end silicone watchband is in a straight state.

Please refer to FIGS. 1 and 2, the present disclosure discloses a smart bracelet with a conductive watchband, which includes a first watchband 2 and a second watchband 3. The first watchband 2 is connected to one end of the dial 1, and the second watchband 3 is connected to the other end of the dial 1. Both the first watchband 2 and the second watchband 3 are formed at one time by hot pressing the silicone. The first watchband 2 is provided with a buckle 21, and the second watchband 3 is provided with several lock holes 31, the lock holes 31 are equally spaced along the length direction of the second watchband 3, and the lock holes 31 are cooperated with the buckle 21. The buckle 21 is aligned and inserted into the corresponding lock hole 31 according to the size of the user's wrist. In order to fix the end of the second watchband 3 to prevent it from lifting, a limiting ring 23 is sleeved on the first watchband 2, and the limiting ring 23 is for inserting the second watchband 3. A clamping block 9 is provided on the outer surface of the first watchband 2, and the clamping block 9 is also cooperated with one of the lock holes 31. The buckle 21 is aligned and inserted into the corresponding lock hole 31, and then the end portion of the first watchband 2 is inserted into the limiting ring 23 after the first watchband 2 is bent. Then, the second watchband 3 is pressed downward so that the clamping block 9 is inserted into the lock hole 31, and the second watchband 3 is further fixed so that the first watchband 2 is in stable contact with the wrist. In one embodiment, the first watchband 2 is a buckle-end silicone watchband and the second watchband 3 is a tongue-end silicone watchband.

Figure 3:
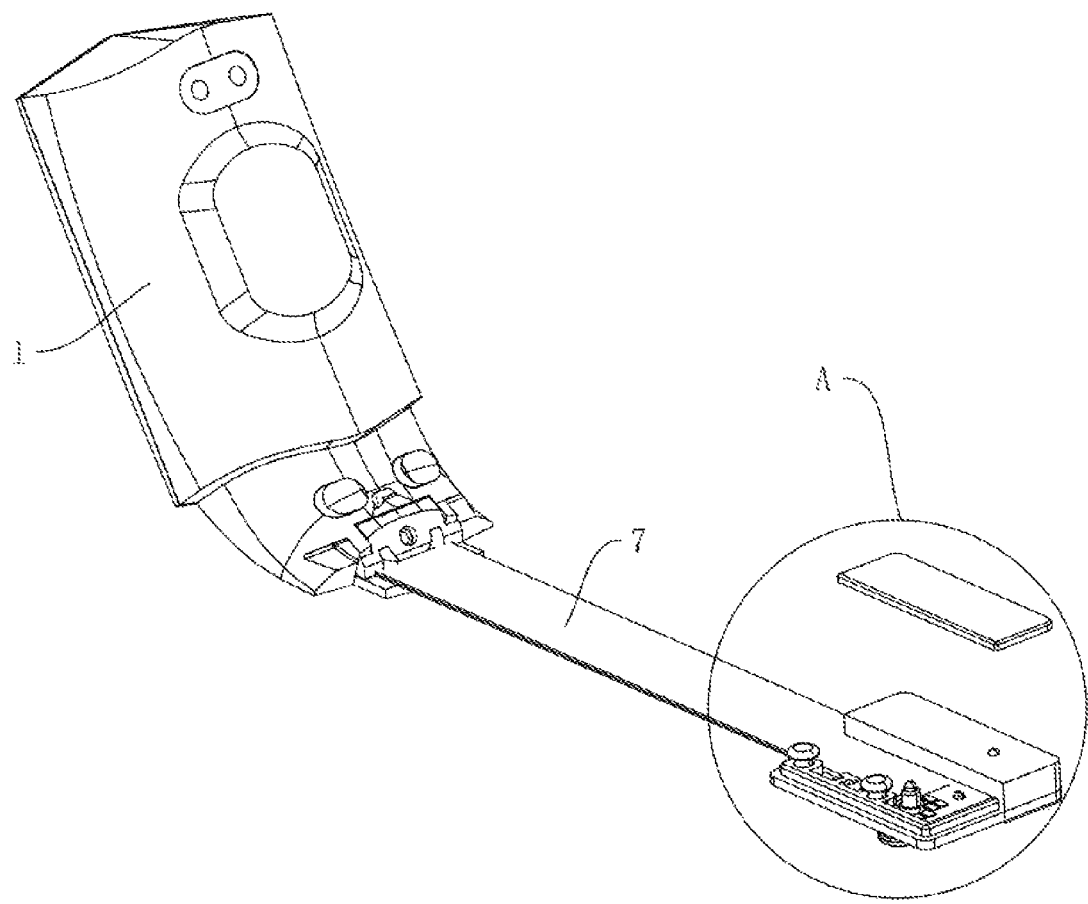
FIG. 3 is a schematic structural diagram showing a part of an electrical stimulation module.
Figure 4:
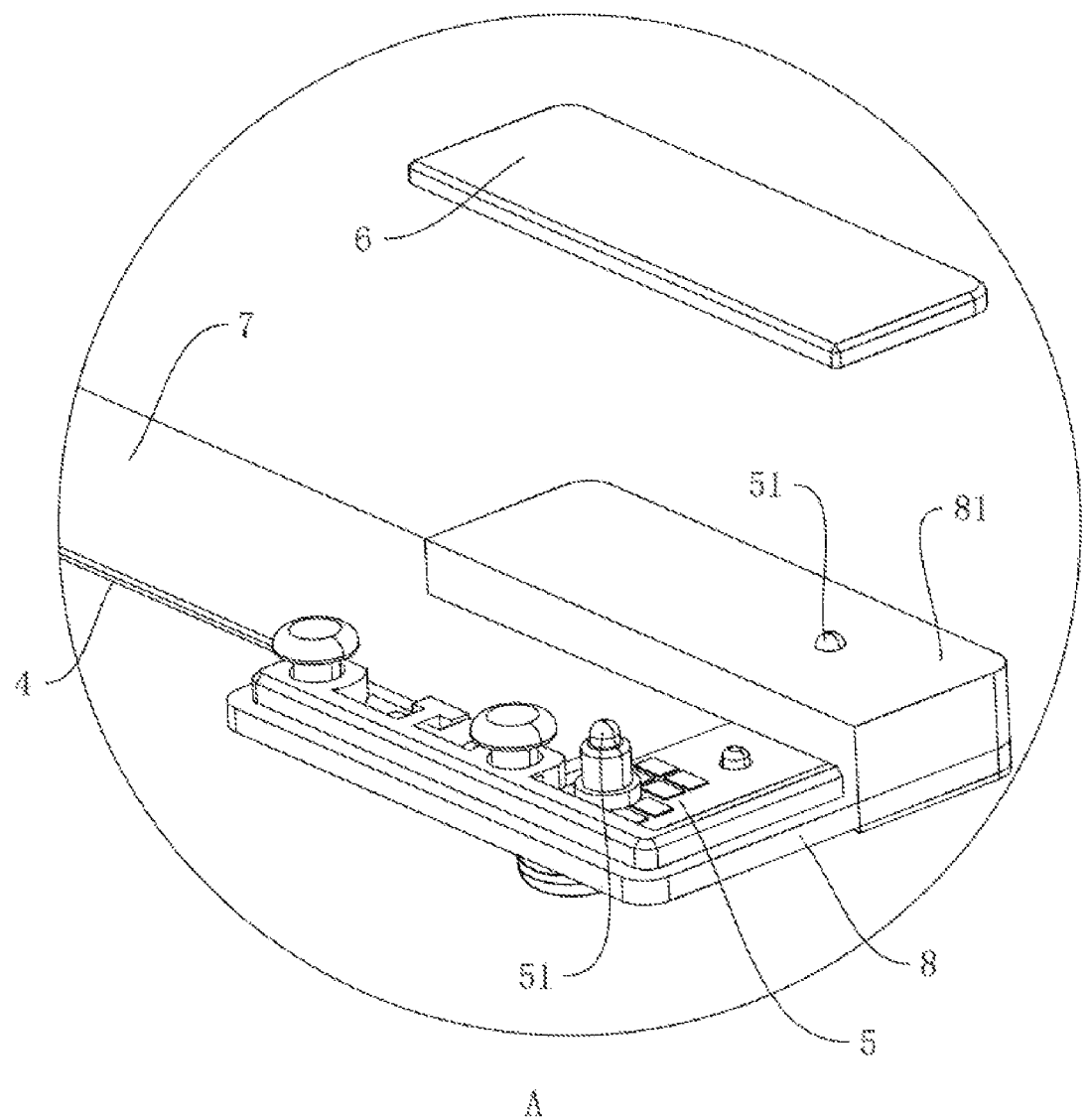
FIG. 4 is an enlarged schematic diagram of part A in FIG. 3.

Please refer to FIGS. 3 and 4, the inside of the buckle-end silicone watchband is provided with an electrical stimulation module, the electrical stimulation module includes a signal strip 4, a circuit board 5 and an electrode 6, the signal strip 4 is arranged along the length direction of the buckle-end silicone watchband, the circuit board 5 is connected to the signal strip 4, the electrode 6 is connected to the circuit board 5, and the electrode 6 is located at the end of the buckle-end silicone watchband away from the dial 1. The end of the signal strip 4 away from the circuit board 5 is connected to the host in the dial 1.

Figure 5:
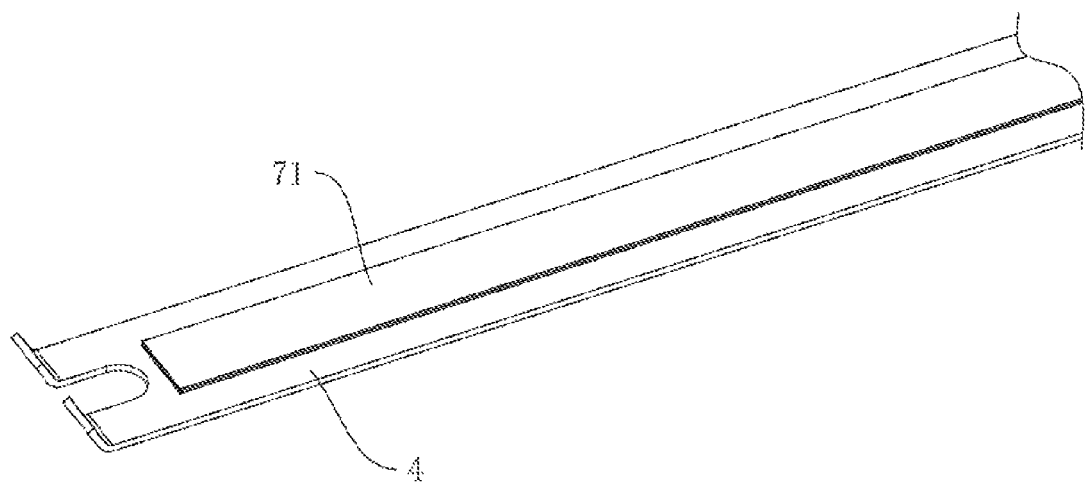
FIG. 5 is a schematic structural diagram showing an insulating layer and a signal strip.

Refer to FIGS. 4 and 5, the inside of the buckle-end silicone watchband is provided with a spring sheet 7 which is arranged along the length direction of the buckle-end silicone watchband, the spring sheet 7 is located directly above the signal strip 4, an insulating layer 71 is spread between the spring sheet 7 and the signal strip 4, and the spring sheet 7, the insulating layer 71, and the signal strip 4 are glued together. The spring sheet 7 increases the elasticity of the buckle-end silicone watchband, and facilitates the bending of the buckle-end silicone watchband. The signal strip 4 is placed inside the buckle-end silicone watchband, which has the characteristics of conductivity, water resistance, and stability, so that the functionality of the watchband is increased. The electrode 6 is installed in the opening at the end of the buckle-end silicone watchband, saving the space of the host of the bracelet. The signal strip 4 embedded in the buckle-end silicone watchband adopts a serpentine pattern to realize the bendability of the buckle-end silicone watchband.

Please refer to FIGS. 1 and 4, the inside of the buckle-end silicone watchband is provided with an electrode support plate 8, and the circuit board 5 is located in the electrode support plate 8, and the spring sheet 7 is located above the electrode support plate 8. The circuit board 5 is provided with a pin 51, the top surface of the electrode support plate 8 is screwed with a bottom carriage 81, the electrode 6 is located on the top surface of the bottom carriage 81, the pin 51 is configured to pass through the bottom carriage 81 and get in touch with the bottom surface of electrode 6. The bottom carriage 81 is made of conductive metal. In this embodiment, the conductive metals such as zinc alloy, stainless steel, and copper can be used. The host of dial 1 sends electrical signal to the signal strip 4, and the signal strip 4 transmits electrical pulse to the circuit board 5, the circuit board 5 transmits the electrical pulse to the electrode 6 through the pin 51, and performs low-frequency pulse electrical stimulation on the wrist acupoints through the electrode 6 to control gastric acid secretion, reduce appetite, convert white fat, and increase metabolism and exercise tolerance, and the host of the bracelet has functions such as step count, exercise data, heart rate, sedentary reminder, countdown, stopwatch, etc. at the same time.

Figure 6:
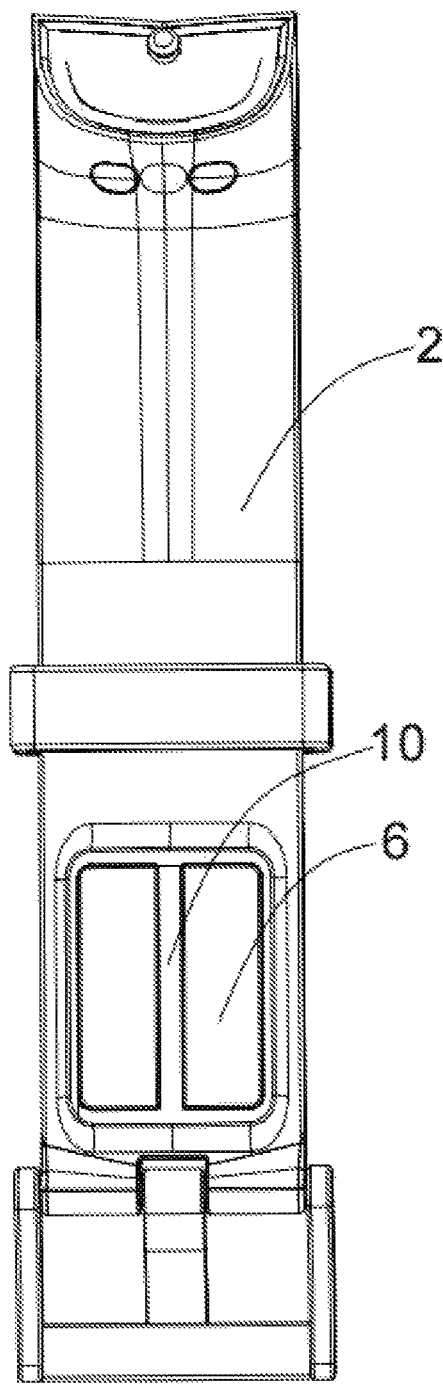
FIG. 6 is a schematic structural diagram of the buckle-end silicone watchband of the First embodiment.

Please refer to FIG. 6, two electrodes 6 are arranged along the width direction of the buckle-end silicone watchband, and a sensor 10 is provided between the two electrodes 6, and the sensor 10 is connected to the circuit board 5. The sensor 10 mainly includes a heart rate sensor for detecting the user's heart rate and a skin resistance sensor for detecting the skin resistance. The two sensors 10 can be used to detect the user's heart rate and skin resistance, the user's current physiological state can be judged through the detected data.

Please refer to FIG. 1, the inner surface of the buckle-end silicone watchband is provided with grooves 22 corresponding to the electrodes 6. There are two grooves 22 and they are arranged symmetrically. A cover plate 61 located above the electrode 6 is provided in the groove 22, and the cover plate 61 is covered over the electrode 6 by hot pressing, and the cover plate 61 is made of conductive metal. In this specific embodiment, the cover plate 61 can be made of conductive metals such as zinc alloy, stainless steel, and copper.

The implementation principle of this embodiment is: when wearing the bracelet, align the buckle 21 and insert it into the corresponding lock hole 31, then insert the end portion of the buckle-end silicone watchband into the limiting ring 23 after bending the buckle-end silicone watchband, then press the tongue-end silicone watchband downward so as to insert the clamping block 9 into the lock hole 31, and the tongue-end silicone watchband is further fixed so that the buckle-end silicone watchband is in stable contact with the wrist.

The host of dial 1 sends electrical signal to the signal strip 4, and the signal strip 4 transmits electrical pulse to the circuit board 5, the circuit board 5 transmits the electrical pulse to the electrode 6 through the pin 51, and performs low-frequency pulse electrical stimulation on the wrist acupoints through the electrode 6 to control gastric acid secretion, reduce appetite, convert white fat, and increase metabolism and exercise tolerance, and the host of the bracelet has functions such as step count, exercise data, heart rate, sedentary reminder, countdown, stopwatch, etc. at the same time.

The signal strip 4 is placed inside the buckle-end silicone watchband, which has the characteristics of conductivity, water resistance, and stability, so that the functionality of the watchband is increased. The electrode 6 is installed in the opening at the end of the buckle-end silicone watchband, saving the space of the host of the bracelet. The signal strip 4 embedded in the buckle-end silicone watchband adopts a serpentine pattern to realize the bendability of the buckle-end silicone watchband.

The Second Embodiment

Figure 7:
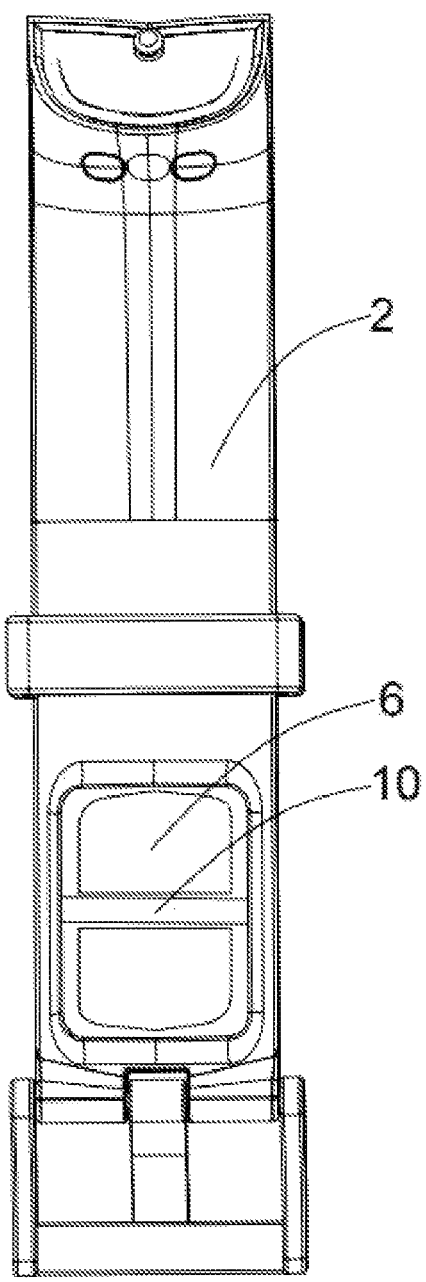
FIG. 7 is a schematic structural diagram of the buckle-end silicone watchband of the second embodiment.

The difference from the first embodiment lies in the distribution of the electrodes 6 and sensors 10, as shown in FIG. 7, in the second embodiment, there are two electrodes 6 arranged along the length direction of the buckle-end silicone watchband, that is, the two electrodes 6 are arranged horizontally and are parallel to each other, and because the arranged position is different, the overall shape of the electrodes 6 are also different to adapt to the installation position, the electrodes are adapted to change. Because the entire watchband is in the shape of a long strip, if it is the same as in the first embodiment, the electrode 6 is in a shape of a long strip with a smaller width and a longer length. However, according to this embodiment, the width of the electrode 6 is made larger and the length is made shorter, and the sensor 10 is also arranged between the two electrodes 6, the sensor 10 also includes a heart rate sensor for detecting the user's heart rate and a skin resistance sensor for detecting the skin resistance. The two sensors 10 can be used to detect the user's heart rate and skin resistance, and the current physiological state of the user can be judged by the detected data.

The implementation principle of this embodiment is the same as that of the first embodiment, and it is not detailed in this embodiment.

The Third Embodiment

Figure 8:
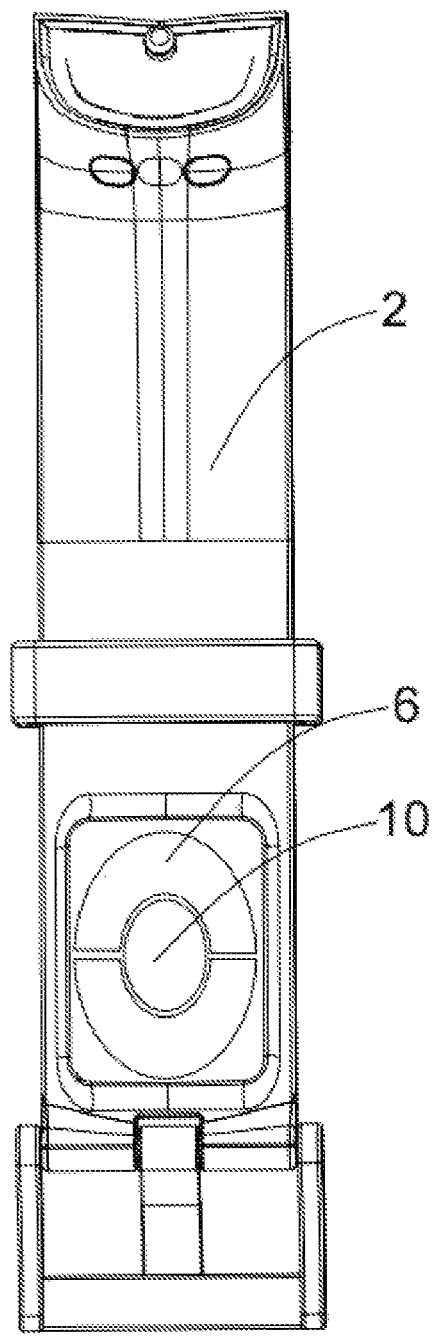
FIG. 8 is a schematic structural diagram of the buckle-end silicone watchband of the third embodiment.

The difference from the first embodiment is that the shape and installation position of the electrodes 6 are different, as shown in FIG. 8, in this embodiment, the electrode 6 has a semicircular ring shape, and the two electrodes 6 can be combined to form a complete ring, and the positions of the two electrodes 6 are distributed up and down, which is similar to the second embodiment, and the sensor 10 is installed in the elliptical area between the two semicircular ring-shaped electrodes 6, the type of sensor 10 is the same as that of the first embodiment, the sensor 10 includes a heart rate sensor for detecting the user's heart rate and a skin resistance sensor for detecting the skin resistance. The two sensors 10 can be used to detect the user's heart rate and skin resistance, and the current physiological state of the user can be judged by the detected data.

The Fourth Embodiment

The difference from the first embodiment is that in the fourth embodiment, the first watchband 2 is a tongue-end silicone watchband, and the second watchband 3 is buckle-end silicone watchband, that is, the electrical stimulation module is stalled on the tongue-end silicone watchband, and the rest of the structure is similar to other embodiments. However, in order to make the electrodes 6 contact the user's wrist, the position of the electrodes 6 may be slightly changed. The two electrodes 6 are respectively arranged on both sides of the lock holes 31 of the tongue-end silicone watchband, when the tongue-end silicone watchband is buckled with the buckle-end silicone watchband, the electrode 6 can still touch the user's wrist after the user wear the bracelet with this structure.

In summary, the beneficial technical effects of the present disclosure are as follows.
1. Through the arrangement of the electrical stimulation module, the signal strip is placed inside the watchband, which has the characteristics of conductivity, water resistance, and stability, so that the functionality of the watchband is increased, the electrode is installed in the opening at the end of the watchband, saving the space of the host of the bracelet, the electrode performs low-frequency pulse electrical stimulation on the wrist acupoints to control gastric acid secretion, reduce appetite, convert white fat, and increase metabolism and exercise tolerance.
2. Through the arrangement of the spring sheet, the spring sheet increases the elasticity of the watchband and further improves the bendability of the watchband.
3. Arrange a sensor between the two electrodes so that the user's physiological data can be directly detected after wearing the bracelet, which further increases the functionality of the watchband.
4. Through the arrangement of the limiting ring, the buckle is aligned and inserted into the corresponding lock hole, and then the end portion of the buckle-end silicone watchband is inserted into the limiting ring after the buckle-end silicone watchband is bent, then the tongue-end silicone watchband is pressed downward so that the clamping block is inserted into the lock hole, and the tongue-end silicone watchband is further fixed so that the buckle-end silicone watchband is in stable contact with the wrist.

It should be noted here that in the description of the present disclosure, it should be understood that the orientation or positional relationship indicated by the terms "length", "width", "upper", "lower", "front", "rear", "left", "right", "vertical", "horizontal", etc. is based on the orientation or positional relationship shown in the drawings, and is only for the convenience of describing the present disclosure and simplifying the description, and does not indicate or imply that the device or element referred to must have a specific orientation, be configured and operate in a specific orientation, and therefore cannot be understood as a limitation of the present disclosure.

The terms "first" and "second" are only used for descriptive purposes, and cannot be understood as indicating or implying relative importance or implicitly indicating the number of indicated technical features. Thus, the features defined with "first" and "second" may explicitly or implicitly include one or more of these features. In the description of the present disclosure, "plurality" means two or more, unless otherwise specifically defined.

The above are only the embodiments of the present disclosure, and do not limit the scope of the present disclosure. Any equivalent structure or equivalent process transformation made using the contents of the specification and drawings of the present disclosure, or directly or indirectly applied to other related art is included in the scope of patent protection of the present disclosure for the same reason.

What is claimed is:

1. A smart bracelet with a conductive watchband, comprising a dial, a first watchband and a second watchband, wherein the first watchband is connected to a first end of the dial, and the second watchband is connected to a second end of the dial; an inside of the first watchband is provided with an electrical stimulation module, and the electrical stimulation module comprises a signal strip, a circuit board and an electrode, wherein the circuit board is connected to the signal strip, the signal strip is arranged along a length direction of the first watchband, one end of the signal strip away from the circuit board is electrically connected with the dial, and the dial is configured to send electrical signal to the signal strip; the electrode is connected to the circuit board, and the electrode is located at an end of the first watchband, wherein the end of the first watchband is away from the dial; the inside of the first watchband is provided with a spring sheet, wherein the spring sheet is arranged along the length direction of the first watchband; and an insulating layer is spread between the spring sheet and the signal strip.

2. The smart bracelet according to claim 1, wherein the spring sheet is located directly above the signal strip.

3. The smart bracelet according to claim 2, wherein the inside of the first watchband is provided with an electrode support plate, the circuit board is located in the electrode support plate, and the spring sheet is located above the electrode support plate.

4. The smart bracelet according to claim 3, wherein the circuit board is provided with a pin, a top surface of the electrode support plate is provided with a bottom carriage, the electrode is located on a top surface of the bottom carriage, the pin is configured to pass through the bottom carriage and get in touch with a bottom surface of the electrode, wherein the bottom carriage is made of conductive metal.

5. The smart bracelet according to claim 1, wherein the first watchband is a buckle-end silicone watchband, the second watchband is a tongue-end silicone watchband, the buckle-end silicone watchband is provided with a buckle, and the tongue-end silicone watchband is provided with a plurality of lock holes, the plurality of lock holes are equally spaced along a length direction of the tongue-end silicone watchband, and the plurality of lock holes are cooperated with the buckle.

6. The smart bracelet according to claim 5, wherein a clamping block is provided on an outer surface of the first watchband, and the clamping block is cooperated with one of the plurality of lock holes.

7. The smart bracelet according to claim 6, wherein a limiting ring is sleeved on the first watchband, and the limiting ring is for inserting the second watchband.

\* \* \* \* \*